(12) United States Patent
Tamsot

(10) Patent No.: US 9,282,885 B2
(45) Date of Patent: Mar. 15, 2016

(54) DEVICE FOR SELECTING CONTACT LENS WITHIN A CABINET ARRANGED TO RECEIVE A PLURALITY OF CONTACT LENS AND METHOD ASSOCIATED THEREOF

(71) Applicant: Ophtalmic Compagnie, Villepinte (FR)

(72) Inventor: Charli Tamsot, Jerusalem (IL)

(73) Assignee: Ophtalmic Compagnie, Villepinte (FR)

( * ) Notice: Subject to any disclaimer, the term of this patent is extended or adjusted under 35 U.S.C. 154(b) by 18 days.

(21) Appl. No.: 14/199,368

(22) Filed: Mar. 6, 2014

(65) Prior Publication Data
US 2014/0307225 A1  Oct. 16, 2014

(30) Foreign Application Priority Data
Mar. 6, 2013 (FR) ...................... 13 52030

(51) Int. Cl.
 *A61B 3/10*  (2006.01)
 *A61B 3/00*  (2006.01)
 *G06Q 10/08*  (2012.01)
(52) U.S. Cl.
 CPC ............ *A61B 3/0025* (2013.01); *G06Q 10/087* (2013.01)
(58) Field of Classification Search
 USPC ................................. 351/200–246
 See application file for complete search history.

(56) References Cited

U.S. PATENT DOCUMENTS

| 8,628,194 B2 * | 1/2014 | Sabeta ..................... 351/159.01 |
| 2010/0181332 A1 * | 7/2010 | Wang et al. ....................... 221/1 |
| 2010/0302509 A1 * | 12/2010 | Steinmuller ................... 351/212 |
| 2011/0054927 A1 | 3/2011 | Renna et al. |

FOREIGN PATENT DOCUMENTS

WO    WO 03/017058 A2    3/2003

OTHER PUBLICATIONS

Search Report for Application No. FR 1352030 dated Sep. 26, 2013.

\* cited by examiner

*Primary Examiner* — Mohammed Hasan
(74) *Attorney, Agent, or Firm* — Alston & Bird LLP

(57) ABSTRACT

The invention relates to a device for selecting contact lenses within a cabinet arranged to receive a plurality of contact lenses, the device including a storage data device, for storing data based on measurements from an auto refractometer; and a data processor device associated with a calculation module for identifying a contact lens on the basis firstly of data from the auto refractometer as previously stored in the storage device and secondly of additional data relating to the contact lens that is to be identified and that was previously input by the user, the data processor device associated with said calculation module also being arranged to identify the location of the lens within the cabinet. The invention also relates to an associated method.

20 Claims, 2 Drawing Sheets

DEVICE FOR SELECTING CONTACT LENS WITHIN A CABINET ARRANGED TO RECEIVE A PLURALITY OF CONTACT LENS AND METHOD ASSOCIATED THEREOF

FIELD

The invention relates to a device for selecting contact lenses within a cabinet, and also to an associated method.

BACKGROUND

When an ophthalmologist examines a patient, an auto refractometer is used to determine the nature of the patient's ametropia (defective vision). The auto refractometer is generally connected to the ophthalmologist's personal computer, which computer includes software capable of processing the data from the refractometer and serving in particular to display the measurements taken by the auto refractometer. An example of software that is in widespread use for this purpose is the StudioVision software available from the supplier RealVision.

Typically, the various kinds of ametropia are as follows: myopia, hyperopia, astigmatism, and presbyopia.

The measurements performed by the auto refractometer are objective measurements. For each eye of the patient, they provide in particular the following conventional data as determined by the above-mentioned software:

- sphere (depending on its sign, this measurement relates to the degree of myopia or of hyperopia of the eye in question of the patient;
- cylinder (a measurement relating to the degree of astigmatism;
- axis (a measurement relating to the axis of astigmatism);
- addition (a measurement relating to the presbyopia correction for progressive lenses; specifying values to be added to far vision in order to provide a correction for near vision);
- radius (radii) (measured relative to the radius of curvature of the cornea of the patient's eye. In general, two radii of curvature of the cornea are measured in order to determine the maximum keratometry and the minimum keratometry), and in general, the following additional data:
  - the axis of the or each radius of curvature of the cornea involved in the measurement.

On the basis of these objective measurements, the ophthalmologist generally carries out subjective evaluation seeking to adapt the objective data supplied by the auto refractometer. This adaptation seeks to take account of the daily lifestyle of the patient, such as daily exposure to light, nature of the patient's work, or the sporting activity of the patient.

Thereafter, the ophthalmologist determines the characteristics of the contact lenses that are to be proposed to the patient.

For this purpose, the ophthalmologist takes account of the nature of the patient's ametropia, as determined by the auto refractometer, in order to select the shape of the lens (e.g. spherical, toric, multifocal), that is best suited to the patient.

The ophthalmologist also takes account of the nature of the material from which the contact lens is made (e.g. silicone hydrogel, hydrogel, rigid).

Finally, the ophthalmologist takes account of the frequency with which the lens is to be worn that the ophthalmologist considers as being the best suited to the patient (e.g. lenses on a daily, monthly, bimonthly, or quarterly basis).

The ophthalmologist also takes account of the measurements performed by the auto refractometer, and possibly of any subjective correction to those measurements.

It should be observed that when a subjective evaluation is made on the basis of objective measurements taken by the auto refractometer (as is often the case), the ophthalmologist must personally make corrections to the measurements that have been taken by the auto refractometer.

The ophthalmologist relies on personal experience and/or on equivalence tables that are well known to the person skilled in the art.

For certain contact lenses, this correction is quite easy to do and the ophthalmologist makes a selection based on personal experience.

Nevertheless, this is not true of all contact lenses. For example, the correction is difficult to determine when toric lenses need to be proposed for a patient. Under such circumstances, the ophthalmologist requires a certain amount of time to select the correction that is finally chosen, relying on equivalence tables.

This can lead to a loss of time, and possibly also to error in the subjective correction.

Once all of the characteristics of the contact lenses have been determined, the ophthalmologist takes the lenses in question from a stock. For this purpose, the ophthalmologist generally has a plurality of storage cabinets from various suppliers.

After a certain amount of time, the ophthalmologist must then reorder contact lenses that are no longer available in the ophthalmologist's own stock so that an employee of the supplier can replenish the stock (restocking).

This leads to a loss of time for the ophthalmologist. Furthermore, it is possible for that to lead to errors in the kinds of contact lenses that are to be supplied.

If the ophthalmologist does not make an order, regular visits by the supplier can also serve to achieve restocking, however that is generally not sufficient since the supplier has no idea about which contact lenses are missing.

Restocking contact lenses available on the premises of an ophthalmologist (test lenses) thus leads to difficulties, both for the ophthalmologist and for the ophthalmologist's supplier.

SUMMARY

An object of the invention is to propose a device and/or a method that avoids at least one of the above-specified drawbacks.

To this end, the invention provides a device for selecting contact lenses within a cabinet arranged to receive a plurality of contact lenses, the device being characterized in that it comprises:

- means for storing data based on measurements from an auto refractometer; and
- data processor means associated with a calculation module for identifying a contact lens on the basis firstly of data from the auto refractometer as previously stored in the storage means, and secondly of additional data relating to the contact lens that is to be identified and that was previously input by the user, said data processor means associated with said calculation module also being arranged to identify the location of the lens within the cabinet.

The device of the invention may also include one or more of the following characteristics, taken singly or in combination:

means for identifying information relating to the content of a box including a contact lens in the identified location in the cabinet, which means are associated with a module for taking account of this data within the device;

remote transmission means for taking information relating to the contact lens for which the box has been identified and transmitting it remotely, e.g. via the Internet; and a remote computer server capable of communicating with the means for remotely transmitting the information relating to the contact lens, the server being arranged to keep track of the contact lenses extracted from the cabinet;

the calculation module is incorporated in the remote computer server;

the calculation module is housed in the cabinet;

display means for displaying said additional data relating to the contact lens, which data includes data to be supplied by a user concerning the shape of the lens, the nature of the material forming the lens, and the frequency with which the lens is to be worn;

communications means, such as a Bluetooth® link, for communicating with a personal computer of the user, which computer stores the data from the auto refractometer;

the cabinet has a plurality of drawers, each drawer being arranged to receive a plurality of series of contact lenses of a given model so that each series of contact lenses differs from another series of contact lenses by its ophthalmic correction power;

the cabinet is in the form of an automatic dispenser of contact lens boxes;

the dispenser cabinet includes means for automatically extracting the box containing the contact lens from its location, e.g. an electric trigger capable of extracting said box and associated with a chute capable of transferring said box to an outlet of the cabinet;

the means for identifying information relating to the content of a box containing the contact lens, e.g. a radio frequency identification (RFID) reader or a bar code reader, are arranged inside the cabinet, advantageously at an outlet from the cabinet;

the dispenser cabinet may include an inlet, e.g. in the form of a slot, for inserting a contact lens box;

the dispenser cabinet may include other means for identifying information relating to the content of a box that includes the contact lens, which means are advantageously arranged inside the cabinet at the inlet to the cabinet;

the dispenser cabinet includes means for putting the box back in its location;

the data processor means associated with the calculation module are also arranged to determine the characteristics of a new lens from the characteristics of a previously identified lens and from additional data measured by the user on a patient wearing said previously identified lens, the additional data comprising at least a measurement of over refraction, said data processor means associated with said calculation module also being arranged to identify the location of this new lens within the cabinet;

when said previously identified lens is a spherical lens, the data processor means associated with the calculation module are arranged to determine the sphere, the cylinder, and the axis of the new lens on the basis of the characteristics of the previously identified lens and of a measurement of over refraction performed on the patient wearing said previously identified lens;

when the previously identified lens is a toric lens, the data processor means associated with the calculation module are arranged to determine the sphere, the cylinder, and the axis of the new lens from the characteristics of the previously identified lens and from measurements of over refraction and of rotation performed by the user on the patient wearing said previously identified lens; and when the previously identified lens is a progressive lens, the data processor means associated with the calculation module are arranged to determine the sphere and/or the addition of the new lens from the characteristics of the previously identified lens, in particular its addition, from the age of the patient, and from over refraction, duochrome, and near and far vision visual acuity measurements, and from a determination of the dominant or fellow eye of the patient performed by the user on the patient wearing the previously identified lens.

For this purpose, the invention also provides a method of selecting contact lenses within a cabinet, which method is characterized in that the following steps are performed:

a) storing data based on measurements from an auto refractometer;

b) inputting additional data relating to the contact lens, other than the data provided by the auto refractometer, namely data relating to the shape of the lens, to the nature of the material forming the lens, and to the frequency with which the lens is to be worn;

c) determining the characteristics of a contact lens available from the supplier on the basis firstly of measurement data from the auto refractometer that has previously been stored, and secondly from additional data previously input by the user in step b);

d) identifying the location of the contact lens within the cabinet; and e) extracting the box including the contact lens from the cabinet.

The method of the invention may also include one or more of the following characteristics, taken singly or in combination:

the method further comprises the following steps:
  f) at least measuring over refraction on a patient wearing the contact lens of characteristics that were determined at step c);
  g) determining the characteristics of the new contact lens on the basis firstly of the measurement data obtained in step f) and secondly of the characteristics of the contact lens as determined in step c);
  h) identifying the location within the cabinet (1) of the new contact lens; and
  i) extracting from the cabinet (1) the box containing the new contact lens;

when the contact lens of characteristics that were determined in step c) is a spherical lens, step g) consists in determining the sphere, the cylinder, and the axis of the new contact lens;

when the contact lens of characteristics that were determined in step c) is a toric lens, step f) consists at least in measuring over refraction and rotation, and step g) consists in determining the sphere, the cylinder, and the axis of the new contact lens;

when the contact lens of characteristics that were determined in step c) is a progressive lens, step f) consists in performing over refraction, duochrome, and near and far vision visual acuity measurements, in determining the dominant or fellow eye of the patient, and in providing the age of the patient, and step g) consists in determining the sphere and/or the addition of the new contact lens;

a step of informing the user of the location of the contact lens within the cabinet;

a step consisting in automatically dispensing the box including the contact lens;

a step in which information contained on the box of the contact lens is identified, said box being provided with a bar code or with an RFID chip;

a step in which the information identified on the contact lens box is transmitted remotely, e.g. via the Internet, in order to enable the contact lenses to be restocked;

a step in which restocking of contact lenses is initiated when the number of boxes including identified contact lenses as transmitted remotely drops below a predefined threshold value; and a step in which the characteristic data of the lens including the information present on the box that has been identified is transmitted to the user's personal computer.

BRIEF DESCRIPTION OF THE DRAWINGS

The invention can be better understood and other objects, advantages, and characteristics thereof appear more clearly on reading the following description that is made with reference to the accompanying drawings, in which.

Figure 1:
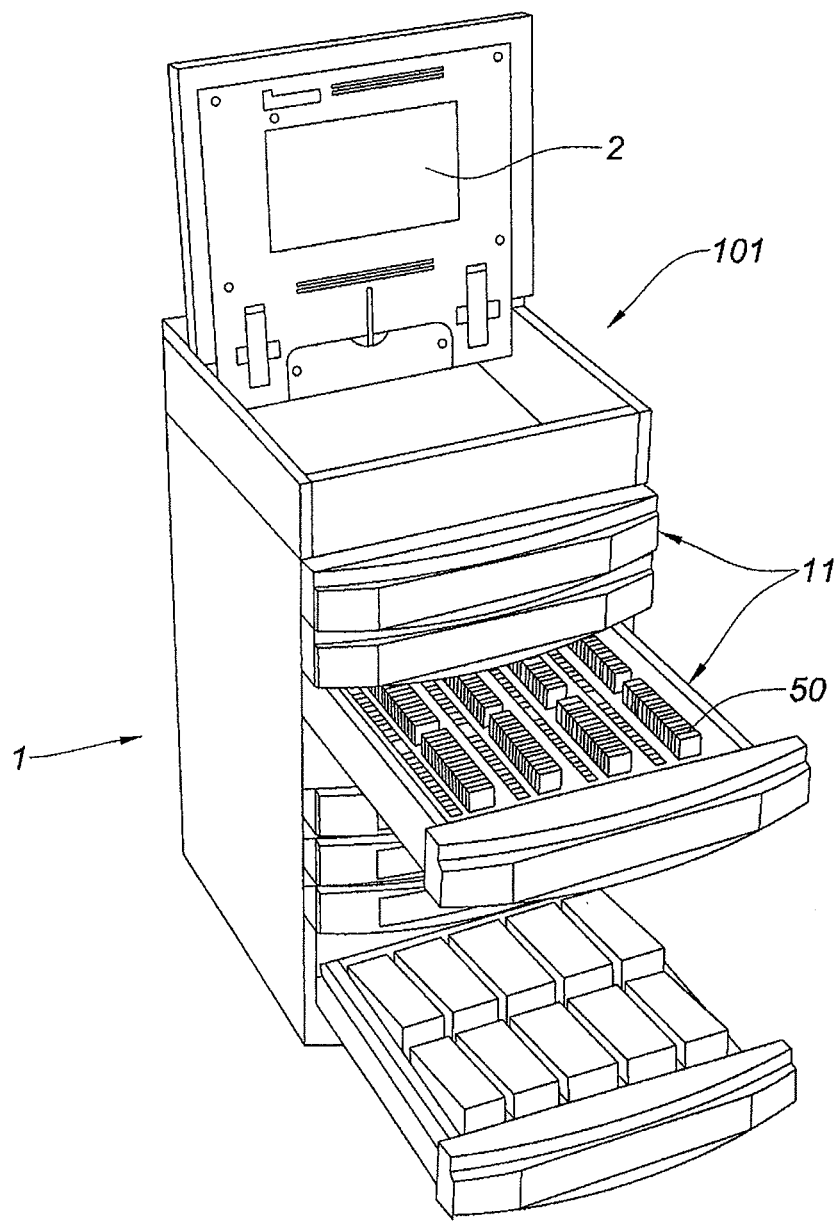
FIG. 1 shows a device in accordance with the invention.
Figure 2:
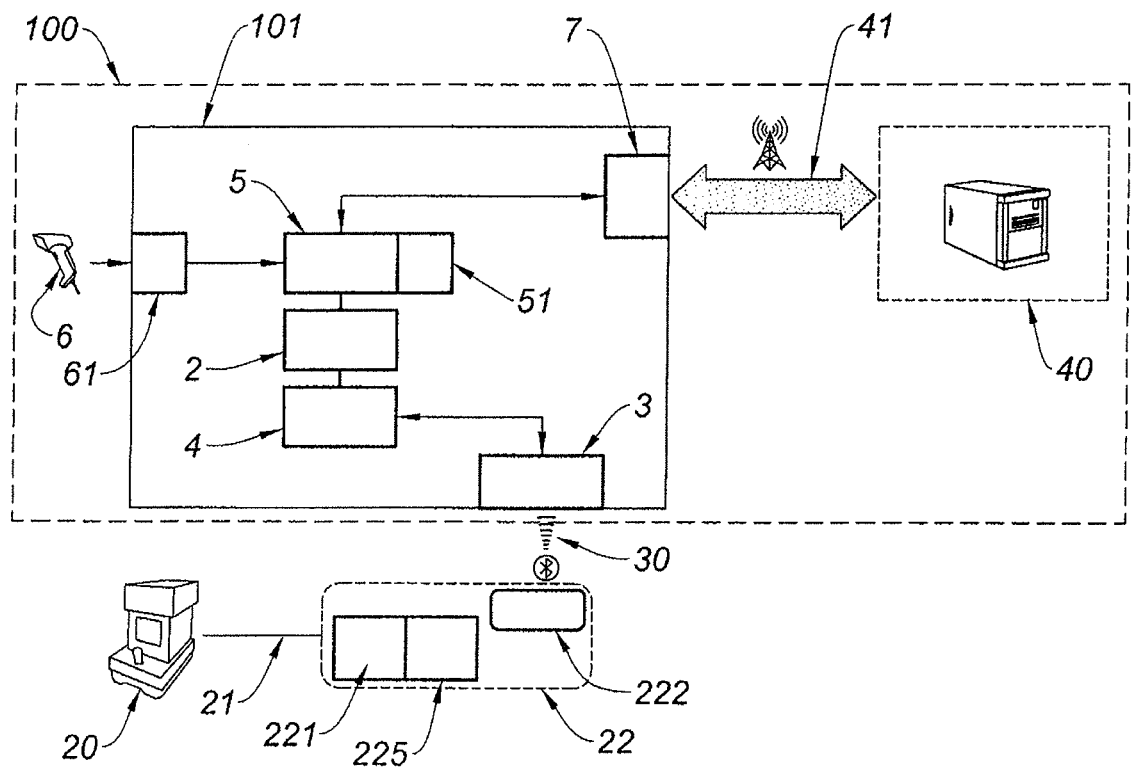
FIG. 2 is a block diagram of the device shown in FIG. 1, together with its environment.

An example of a device for selecting and restocking contact lenses in accordance with the invention is shown in FIG. 1 and FIG. 2.

The device 100 comprises a portion 101 installed locally with an ophthalmologist and a remote portion 40 installed with a supplier.

The portion 101 is in the form of a cabinet 1 arranged to receive a plurality of contact lenses 50 and housing a plurality of functions as described below.

DETAILED DESCRIPTION

The auto refractometer 20 is generally connected by a cable 21 to the personal computer 22 of the ophthalmologist. The personal computer 22 includes software 221 for processing data coming from the auto refractometer 20, and a memory 225 for storing the data as processed in this way.

In order to provide communication between the ophthalmologist's personal computer 22 and the device in accordance with the invention, it is possible to use a module 222 of the computer 22 for managing a Bluetooth® link 30. Under such circumstances, the device 100 likewise has a module 3 for managing a Bluetooth® link, for the purpose of communicating with the software 221 for processing the data from the auto refractometer 20 and/or for communicating with the memory 225.

The data from the software 221 can thus be transferred into the device 100 in accordance with the invention and stored therein.

For this purpose, the device 100 includes storage means 4 (memory) for storing the measurement data from the auto refractometer 20. The storage means 4 may advantageously be a flash memory storing data temporarily for subsequent processing.

The Bluetooth® link is merely an example, and it is possible to envisage using other modes of communication between the ophthalmologist's personal computer 22 and the device 100 in accordance with the invention, such as a WiFi link or a wired link using a local network.

It is even possible to envisage having no mode of communication between the ophthalmologist's personal computer 22 and the device 100 of the invention. Under such circumstances, the display means 2 of the device may provide for displaying a keypad to enable the ophthalmologist to key in directly the data from the auto refractometer. In a variant, the device 100 could have a keypad for this purpose.

In any event, the display means 2 serve to display data relating to the lens. In particular, the display means 2 serve to display a window proposing information about selecting the contact lens that the ophthalmologist is indeed seeking to select, this information being additional to the information supplied by the auto refractometer 20.

This information relates in particular to the frequency with which the contact lens is to be worn (daily, monthly), the nature of the material from which the contact lens is made and the shape of the contact lens (spherical, toric, . . . ).

The device 100 also has data processor means 5 such as a processor or a set of processors associated with a calculation module 51 serving to determine which contact lens is the most appropriate for the patient.

For this purpose, the calculation module 51 relies on measurements from the auto refractometer 20 (sphere, cylinder, axis, addition, radius (radii), and optionally but not necessarily about the axis associated with the or each radius), which measurements are previously stored in the memory 4. The calculator module also relies on information displayed on the display means 2 (shape of the contact lens, nature of the material forming the lens, frequency with which the lens is to be worn), as requested of the ophthalmologist and as previously entered into the device 100 by the ophthalmologist.

In a basic version, the calculation module 51 thus has the following data input thereto:

the shape of the contact lens (associated with the type of ametropia), the nature of the material forming the lens, and the frequency with which the lens is to be worn; as input by the ophthalmologist directly into the device 100; and sphere, cylinder, axis, addition, and two measurements of radii of curvature of the cornea (keratometry max and min); obtained from the auto refractometer 20 and possibly corrected subjectively by the ophthalmologist.

With the above-specified input data, the calculation module 51 determines which contact lens is the best adapted to the vision defect of the patient, using the following criteria:

1) shape of the lens (ametropia): exact match;

2) material of the lens: exact match;

3) frequency with which the lens is to be worn: exact match; and 4) radius: identifying the radii that are available from the supplier.

The extreme values for radii available from the supplier for "standard" contact lenses serve to define a range $[R_{min}, R_{max}]$. This range $[R_{min}, R_{max}]$ depends on the supplier's product range and may vary over time for each supplier.

The radius must then lie within the minimum and maximum values $[R_{min}, R_{max}]$ for this radius that are available in the "standard" range of lenses proposed by the supplier.

On the (rare) assumption that the ophthalmologist makes only one measurement of this radius of curvature, it is possible to select this measurement directly, which measurement may be objective or subjective as explained above.

In the more usual situation where the ophthalmologist takes two measurements of the radius of curvature of the cornea (keratometry max, keratometry min), this radius is determined as a function of these two measurements of the radius of the curvature of the cornea, and possibly also of the sphere, as obtained from the auto refractometer 20.

For example, it is possible to determine the radius by taking the arithmetic mean between the two radius measurements performed with the auto refractometer. Thereafter, it is verified whether this radius lies within the range $[R_{min}, R_{max}]$. If so, an appropriate lens can be found.

5) sphere: identifying a sphere value available from the supplier.

The extreme sphere values available from the supplier of standard contact lenses serve to define a range [SphereMin, SphereMax].

If the sphere value lies within this range and corresponds to an exact value available in the supplier's product range, then this lens is selected (trivial situation).

If this sphere value lies within the range [SphereMin, SphereMax], but the exact value of this sphere as obtained from the auto refractometer, in objective or subjective form is not identified as forming one of the standard contact lenses available with the supplier, then:
- if the sphere value (obtained from the auto refractometer measurement) is negative, a contact lens that is available in the supplier's product range is selected as a function of the nearest smaller value, in absolute value, for this sphere;
- if the sphere value (obtained from the auto refractometer measurement) is positive, then a contact lens that is available in the supplier's product range is selected as a function of the nearest greater value, in absolute value, for this sphere.

6) cylinder: identifying a cylinder value available from the supplier.

The extreme sphere values available from the supplier for standard contact lenses makes it possible to define a range [CylMin, CylMax].

If the value of the cylinder lies within this range and corresponds to an exact value available from the supplier's product range, then this lens is selected (trivial situation).

If this cylinder value lies within the range but the exact value is not identified as being one of the lenses available in the supplier's product range, then a contact lens is selected as a function of the nearest smaller value, in absolute value, of the cylinder.

7) axis (astigmatism): identifying an axis value available from the supplier.

The extreme axial values available from the supplier for standard contact lenses make it possible to define a range [AxisMin, AxisMax].

If the axis value lies within the range and corresponds to an exact value available in the supplier's product range, then this lens is selected (trivial situation).

If the axis value lies within the range but the exact value is not identified as being one of the contact lenses available in the cabinet, then:

If 0<axis<45°, a contact lens is selected from the supplier's product range that presents the axis value that is the nearest to the value zero.

If 45°≤axis<135°, then a contact lens is selected having the axis value that is the nearest to 90°.

If 135°≤axis<180°, then the contact lens is selected that presents the axis value nearest to 180°.

8) addition: several circumstances need to be distinguished.

If the contact lens presents a single addition profile, then that addition profile is selected (trivial situation).

If the contact lens presents two addition profiles (low profile=first addition value, high profile=second addition value, greater than the first addition value):
- either the addition is less than or equal to a predefined threshold value (e.g. threshold value=2.25 diopters), in which case the low profile is selected;
- or else the addition is strictly greater than the threshold value, in which case the high profile is selected.

If the contact lens presents more than two addition profiles, then:
- if the addition is strictly less than the threshold value (e.g. threshold value=2.25 diopters), then the contact lens that satisfies this criterion is selected;
- if the addition is equal to the threshold value or greater, then an addition of predetermined value is added to the sphere that has been obtained in order to select the contact lens (for an addition of value 2.25, the predetermined value to be added to the sphere is 0.25; for an addition of value 3, then the predetermined value to be added to the sphere is 0.5).

The most appropriate contact lens (test lens) is advantageously determined by complying with the above order 1) to 8). Thus, once condition 1) is satisfied, a search is made for a contact lens available in the supplier's product range that is capable of satisfying condition 2), and so on for all of the conditions. Nevertheless, it is possible to envisage using some other order when selecting a contact lens.

This is particularly advantageous since it avoids any need for the ophthalmologist to call on personal experience, or in certain circumstances to use equivalence tables as are well known to the person skilled in the art for matching data relative to corrective lenses for eyeglasses with the corresponding data for contact lenses.

The data processing is thus faster and less subject to possible errors of assessment by the ophthalmologist.

Furthermore, once the most appropriate contact lens for the patient has been determined, the processor means 5 associated with the calculation module 51 also serve to identify the location within the cabinet 1 of the contact lens.

The processing performed thus makes it possible not only to select the characteristics of the contact lens that is the most appropriate for the patient, but also serves to identify the drawer 11 in the cabinet 1 that contains the lens.

The display means 2 can then be used to display the position of the lens in the cabinet. In a variant, in addition to having only a visual alert that consists in displaying the location of the looked-for lens on the display means, it is possible to envisage having an audible alert and/or a visual alert.

If the contact lens that is likely to be the most appropriate for the patient does not satisfy one of the criteria defined by above references 1) to 8), that means the contact lens does not exist in the standard product range of contact lenses available from the supplier. Under such circumstances, the ophthalmologist needs to order a made-to-measure lens (a contact lens Rx) from the supplier.

Furthermore, after using the calculation module 51 to determine the most appropriate contact lens for the patient, it is possible that the lens is indeed present in the range of standard contact lenses available from the supplier, but that the cabinet 1 is not arranged to provide for this contact lens. For reasons of efficiency, the cabinet 1 preferably contains the lenses that are prescribed the most. Under such circumstances, the ophthalmologist must likewise order this standard contact lens from the supplier.

Nevertheless, in a particularly advantageous embodiment, it is appropriate to recall that the invention also seeks to avoid the cabinet 1 being out of stock of standard contact lenses for which locations are initially provided in the cabinet.

To this end, the device 100 may include means 6 for identifying the box containing the previously selected and identified contact lens. These means 6 may be a bar code reader or an RFID reader. To this end, advantage is taken of a bar code or of an RFID chip present on each box of contact lenses.

FIG. 2 shows a bar code reader 6 that can be handled by the ophthalmologist.

With an RFID reader, it is possible to envisage incorporating the reader directly in the cabinet 1. The ophthalmologist then needs to pass the box of contact lenses fitted with an RFID chip in front of the RFID reader. Advantageously, each drawer 11 of the cabinet 1 is provided with a reader of this type, such that it is possible for a box of contact lenses to be identified automatically each time it leaves the drawer 11 in question. Once the box has been identified, a module 61 that also forms part of the device 100 and that is connected to the identification means 6 serves to take account of the information in the bar code.

Taking account of the information identified on the box enables the data processor means 5 of the device to perform several actions that are particularly advantageous.

Firstly, by using a module 7 and a remote link 41, such as the Internet, this enables the data identified on the lens box to be transmitted to a remote computer server 40 located with the contact lens supplier.

As a result, the contact lens supplier knows which lens has been used by the ophthalmologist. This enables restocking to be managed effectively, with knowledge of the various contact lenses remaining in the cabinet 1 present in the ophthalmologist's office. The supplier can then identify which contact lenses are likely to be missing and can organize targeted delivery. This avoids any need for the ophthalmologist to make an order, thereby saving time. This also makes it possible to avoid possible errors that the ophthalmologist might make when making an order.

Secondly, the device 100 can send the data received by the module 61 to the ophthalmologist's personal computer 22 via the above-mentioned link 30. A file 224 taking account of all of the characteristics of the contact lens proposed by the ophthalmologist is thus stored with the initial file 223 relating to the patient. It is thus possible to track variation in the types of contact lens proposed in succession to the patient.

Figure 3:
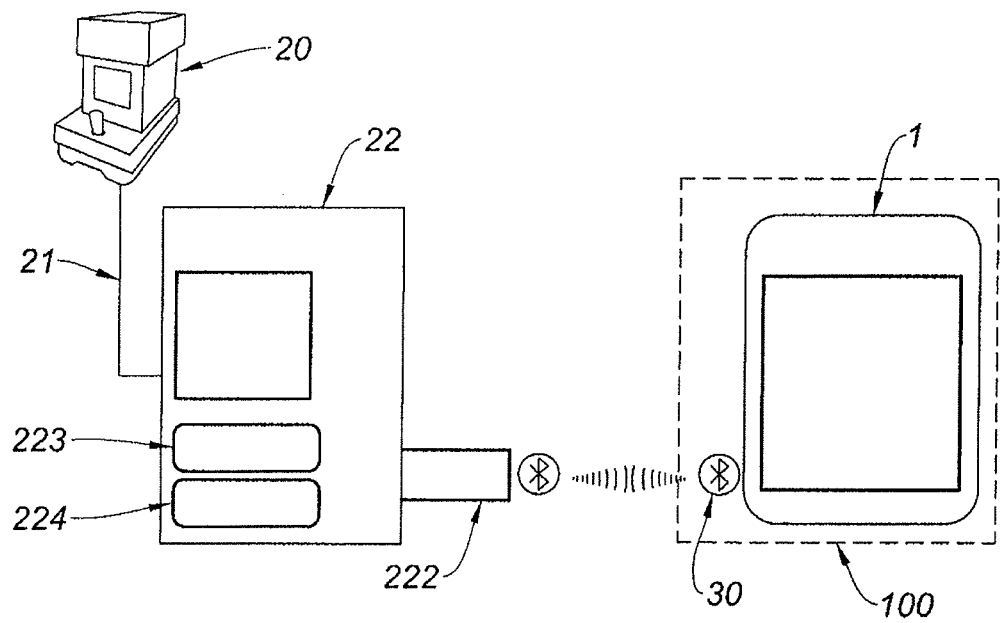
FIG. 3 is another functional block diagram of the device shown in FIG. 1.

On this topic, reference may be made to FIG. 3.

The fact of scanning the lens box produces traceability that makes it easy to identify a batch of faulty contact lenses.

If the ophthalmologist seeks to put back the contact lens box that has been extracted from the cabinet, the box can be identified once again with the means 6 in order to avoid the stock being decremented.

It should be observed that the data from the auto refractometer 20, as processed by the software 221 and stored in the memory 225 of the ophthalmologist personal computer 22 may be objective data concerning measurement actually performed by the auto refractometer. The data may also be subjective data, i.e. data that the ophthalmologist has modified personally on the basis of the objective data provided by the auto refractometer 20. Either way, the objective or subjective data is organized in the ophthalmologist's personal computer 22 with the help of the software.

This aspect does not change in any way the operation of the device 100 in accordance with the invention, which can thus receive equally well data that is objective or subjective, which data is based in both situations on measurement data from the auto refractometer 20.

It should also be observed that the calculation module 51 is advantageously incorporated within the device 100, i.e. on the premises of the ophthalmologist. Nevertheless, in a variant it is possible to envisage incorporating the calculation module 51 in a remote server 40. However this variant is less advantageous since it relies on the remote connection 41 functioning properly.

Furthermore, the above description assumes that it is the ophthalmologist who inputs data relating to the shape of the contact lens (associated with ametropy), to the nature of the material forming the lens, and to the frequency with which the lens is to be worn, by acting on the display means 2 present in the device 100.

However, in some circumstances, the ophthalmologist's personal computer 22 provides a user interface enabling the ophthalmologist to input this data. Under such circumstances, the device 100 acting via the processor means 5 and the calculation module 51 can initiate calculation of the contact lens that is the most appropriate for the patient directly on the basis of the data transmitted from the ophthalmologist's personal computer 22 to the device 100. Under such circumstances, the display means 2 are not necessary.

The cabinet 1 described above with reference to the accompanying figures is a piece of furniture 1 having drawers 11.

In a variant (not shown in the accompanying figures), it is possible to envisage the cabinet 1 being a piece of furniture in the form of an automatic dispenser of contact lens boxes. The operation of a device in accordance with the invention including such a cabinet, referred to below as a dispenser cabinet, is similar to that described for the different variants above, concerning the transfer of data between the ophthalmologist's personal computer 22 and the device 100, concerning storage in the memory 4, and concerning the selection of contact lenses by using the processor means 5 and the associated calculation module 51.

In contrast, with such a dispenser cabinet, the means for identifying the information contained on a contact lens box are different.

Furthermore, a dispenser cabinet also has means for automatically extracting the box corresponding to the lens selected by the calculation module 51. For this purpose, the contact lenses are arranged in the dispenser cabinet in a manner analogous to their arrangement in the cabinet 1 with drawers.

Each level of the dispenser cabinet can then be considered as corresponding to a drawer 11 of the cabinet 1 shown in FIG. 1. In other words, the dispenser cabinet may be arranged to receive a plurality of series of contact lenses of a given model on each of its levels, with each series of contact lenses differing from another series of contact lenses in the power of its ophthalmic correction. From one level to another, it is possible to provide different models of lenses.

Means are then provided for extracting a contact lens box. For example, such means may comprise an electrical trigger capable of extracting the box in question from its location, and associated with a chute capable of transferring the box that has been extracted from its location and conveying it to the outlet from the dispenser cabinet.

The means (first reader) for identifying the information contained on the box (e.g. an RFID or a bar code reader) are then advantageously installed inside the dispenser cabinet, preferably at the outlet from the cabinet from which the ophthalmologist can retrieve said box. In a variant, this reader may be arranged inside the cabinet and not at its outlet, or it may be arranged on the outside portion of the cabinet, or indeed outside the cabinet, as shown in FIG. 2.

The transfer, if any, of the information recovered by the reader to the remote server 40 then takes place as described above for the device 100 described with reference to FIGS. 1 to 3, as does the transfer, if any, of this information to the ophthalmologist's personal computer 22.

If the ophthalmologist seeks to return the box that has been extracted from the dispenser cabinet (e.g. if the ophthalmologist has made a subjective correction to the objective data from the auto refractometer that seems to be erroneous), it is possible for the box to be inserted into the cabinet via an inlet provided for this purpose, e.g. a slot.

By way of example, means (second reader) for identifying the information contained in an RFID chip or a bar code present on the box are advantageously installed inside the cabinet at said inlet in order to identify the contact lens and thus make sure that it is not decremented from the cabinet. In a variant, this second reader may be arranged inside the cabinet, but not at its inlet, or it may be arranged on an outside portion of the cabinet, or indeed outside the cabinet, as shown in FIG. 2.

Finally, when an inlet is provided to the dispenser cabinet, the cabinet includes means for putting the box back into its place.

The various means of the dispenser cabinet relating to optionally returning a previously extracted contact lens box to its place are optional, but advantageously they are provided.

The invention is not limited solely to the device 100 described above in its different variants.

Thus, the module 51 may have other functions seeking to propose a new test lens after the patient has already been testing for a few hours or a few weeks a test lens that was prescribed by the ophthalmologist. This constitutes a verification step that makes it possible to propose a new contact lens.

Case No. 1: Checking a Spherical Lens

The ophthalmologist selects the previously performed test, or one of such tests, as stored in the memory 4. The list relating to the or each test that has been performed for a patient is displayed on the display means 2 with the corresponding lens being selected by date and name. In general, the ophthalmologist will select the most recent test, which corresponds to the test lens being worn by the patient. All of the characteristic data for the lens is thus known.

In known manner, the ophthalmologist then inputs the value corresponding to the biomicroscopy of the eye in order to indicate whether the lens has appropriate fitting parameters concerning centering, mobility, and coverage. In the event of poor centering or poor coverage, for example, the ophthalmologist may request a call from the supplier's technical support.

Usually there will be no difficulty with positioning the lens.

The ophthalmologist then inputs the parameters corresponding to monocular over refraction for each of the two eyes wearing a respective test lens. To obtain this data, the ophthalmologist takes measurements in conditional manner, while the patient is wearing the test lenses. Over refraction is the refraction obtained on a lens being worn.

The ophthalmologist then enters the measured over refraction data into the device 100 in accordance with the invention, e.g. using the personal computer 22.

With the above-specified input data, the calculation module 51 in association with the processor means 5 determines a new test contact lens that is better adapted, as follows:

sphere=sum of the sphere of the test lens selected by the ophthalmologist (e.g. the lens being worn by the patient) plus the over refraction sphere;

cylinder=over refraction cylinder; and axis (astigmatism)=over refraction axis.

It should be observed that the resulting lens is not necessarily a spherical lens.

Once the calculation has been performed by the module 51, identification and selection of the new test lens take place as described above. In particular, the processor module 5 determines whether the new test lens is available in the cabinet or whether it needs to be ordered.

In summary, when the previously identified lens is a spherical lens, the data processor means 5 associated with the calculation module 51 are arranged to determine the sphere, the cylinder, and the axis of the new lens on the basis of the characteristics of the previously identified lens and on the basis of an over refraction measurement performed on the patient wearing the previously identified lens.

Case No. 2: Checking a Toric Lens

The ophthalmologist selects the previously performed test, or one of them, as stored in the memory 4. In general, the ophthalmologist selects the most recent test, the test that corresponds to the test lens being worn by the patient. All of the characteristic data of this lens is therefore known.

In known manner, the ophthalmologist then inputs values corresponding to biomicroscopy of the eye in order to indicate whether the lens has fitting parameters that are appropriate in terms of centering, mobility, and coverage. In the event of difficulty with positioning the lens, the ophthalmologist may call the supplier's technical support.

Usually, there is no difficulty with positioning the lens.

The ophthalmologist then uses a known method to measure the rotation of each lens.

The ophthalmologist must then determine the parameters that correspond to the monocular over refraction for each of the two eyes wearing a test lens.

Thereafter, the ophthalmologist inputs the rotation measurements and the measurements associated with monocular over refraction into the device 100.

With the above-specified input data, the calculation module 51 together with the processor means 5 can then act as follows to determine a new test contact lens that is better adapted, by determining the sphere, cylinder, and axis parameters that involve the rotation measurements.

sphere=B3+B6+(B4+B7)/2−B13/2;

cylinder=B13;

axis: IF B14≤0.5 THEN axis=INT[B14+180+0.499];
 ELSE axis=INT[B14+0.499];

With:

INT=the mathematical operator giving the integer portion of a number;

B3=the sphere of the selected test lens (e.g. the lens worn by the patient coming for checking);

B4=the cylinder of the selected test lens;

B5=the axis of the selected test lens;

B6=over refraction sphere;

B7=over refraction cylinder;

B8=over refraction axis;

B9=measured rotation of the selected test lens.

And:

B11=B4*COS((B5−B9)*PI/90)+B7*COS(B8*PI/90)

B12=B4*SIN((B5−B9)*PI/90)+B7*SIN(B8*PI/90)

B13=−((B11^2+B12^2)^0.5)

Calculating B14;

---

If B12=0
Then
 If B13−B11=0

```
            Then B14 = 180 − B9
            Else B14 = 90 − B9
            EndIf
        Else
            B14 = B9 + ATAN((B13−B11)/B12)*180/PI
        EndIf
```

Where: PI is approximately equal to 3.14159.

Once the calculation has been performed by the module 51, the new test lens is identified and selected as described above. In particular, the processor module 5 determines whether the new test lens is available in the cabinet or whether it needs to be ordered.

In summary, when the previously identified lens is a toric lens, the data processor means 5 associated with the calculation module 51 are arranged to determine the sphere, the cylinder, and the axis of the new lens on the basis of the characteristics of the previously identified lens and of over refraction and rotation measurements performed by the user on the patient wearing the previously identified lens.

Case No. 3: Checking a Progressive Lens

The ophthalmologist selects the previously performed test, or one of them, as stored in the memory 4. In general, the ophthalmologist selects the most recent test, which corresponds to the test lens being worn by the patient. All of the data characteristic of this lens is thus known.

In known manner, the ophthalmologist then inputs the values corresponding to the biomicroscopy of the eye in order to indicate whether the lens has fitting parameters that are suitable in terms of centering, mobility, and coverage. In the event of difficulty in positioning the lens, the ophthalmologist may call the supplier's technical support.

Usually, there is no difficulty in positioning the lens.

The ophthalmologist then inputs the patient's dominant eye into the device 100, i.e. the left eye or the right eye. By definition, the fellow eye is the non-dominant eye. More precisely, the fellow eye or the more convex eye is the eye for which the sphere of the selected test lens for determining the new test lens is the greatest in algebraic value.

The ophthalmologist also inputs the patient's age into the device 100.

Thereafter, the ophthalmologist inputs into the device 100 the patient's preference concerning the red/green test in far vision: red, green, or balance.

The "green" value causes an alert window to appear, informing the ophthalmologist that it is necessary to modify the correction so that it tends towards red.

The ophthalmologist must then input into the device 100 values for binocular visual acuity, while the patient is wearing the selected test lens:

far vision visual acuity (FVVA): a scrolling list is displayed in which the values are labeled on the Monoyer visual acuity scale. In the scrolling list, the size of the font used increases with decreasing acuity in order to make the scale more readable; and near vision visual acuity (NVVA): a scrolling list is displayed in which the values are labeled on the Parinaud visual acuity scale. The size of the font used in the scrolling list increases with decreasing acuity in order to make the scale more readable. It is also necessary to specify the distance at which the test is performed.

The calculation module 51 then operates as follows on the basis of the data input into the device 100 by the ophthalmologist, e.g. using the personal computer 22.

The calculation module 51 is based on defining a score taken from the Monoyer scale (FVVA) and the Parinaud scale (NVVA), as follows:

For FVVA:
12/10=8 points
11/10=7 points
10/10=6 points
9/10=5 points
8/10=4 points
7/10=3 points
6/10=2 points
5/10=1 point For NVVA:
P2=8 points
P3=6 points
P4=4 points
P5=2 points The score is then defined as the sum of the points obtained for FVVA and NVVA.

If the score≥12, then the following level 1 algorithm is used, being performed by the calculation module 51.

If FVVA≥10/10, then the sphere of the fellow eye is increased by +0.25 diopters;

If FVVA≤9/10 and NVVA≥P3, then the sphere of the dominant eye is decreased by −0.25 diopters;

If both eyes are "low" and 52 years≤patient's age≤55 years, then the addition of the fellow eye is increased from "low" to "high" (where "low" and "high" are terms well known to the person skilled in the art);

If the fellow eye is already "low" and patient's age>55 years and FVVA≥10/10, then the addition of the dominant eye is increased from "low" to "high"; and If none of the above four conditions apply, then the level 3 algorithm is used.

If 9<score<12, then the following level 2 algorithm is used:

If NVVA>10/10 and duochrome is green and/or over refraction is convex or flat, then the sphere of both selected test lenses is increased by +0.25 diopters;

If FVVA≤8/10 and NVVA>P2 then the sphere of both selected test lenses is decreased by −0.25 diopters; and If neither of the above two conditions applies, then the level 3 algorithm is used.

Finally, if score≤9 or if the level 1 and level 2 algorithms have not reached a solution, then the following level 3 algorithm is used:

If patient's age lies in the range 45 years to 48 years (included), then the sphere (over refraction) of both test lenses is reduced by −0.25 diopters;

If the patient's age lies in the range 48 years (excluded) to 50 years (included), then the sphere of the test lens for the dominant eye is reduced by −0.25 diopters and the sphere for the test lens on the fellow eye is reduced by −0.50 diopters;

If the patient's age lies in the range 50 years (excluded) to 52 years (included), then the sphere of both test lenses is reduced by −0.25 diopters;

If the patient's age lies in the range 52 years (excluded) to 55 years (included), then the sphere on the dominant eye is reduced by −0.50 diopters at "low", and the sphere on the fellow eye is reduced by −0.75 diopters at "high"; and If the patient's age is greater than 55 years, then the sphere on both lenses is reduced by −0.75, with "low" addition on the dominant eye and "high" addition on the fellow eye.

Once the calculation has been performed by the module 51, the new test lens is identified and selected in the same manner as described above. In particular, the processor module 5 determines whether the new test lens is available in the cabinet or needs to be ordered.

In summary, when the previously identified lens is a progressive lens, the data processor means 5 associated with the calculation module 51 are arranged to determine the sphere and/or the addition of the new lens on the basis of the characteristics of the previously identified lens, in particular its addition, on the basis of the patient's age, and on the basis of over refraction, duochrome, and near and far vision visual acuity measurements, and on the basis of determining the dominant or fellow eye of the patient carried out by the user on the patient wearing the previously identified lens.

Under all circumstances (lens that may be spherical, toric, or progressive), the data processor means 5 associated with said calculation module 51 are also arranged to identify the location within the cabinet 1 of the new lens.

The invention also relates to a method of selecting and restocking contact lenses within a cabinet, which method is nevertheless advantageously performed using the device 100.

The method comprises a step a) of storing data based on measurements from an auto refractometer 20.

The method includes a step b) consisting in inputting additional data relating to the contact lens that is to be selected, other than the data supplied by the auto refractometer, namely data relating to the shape of the lens, to the nature of the material from which the lens is made, and to the frequency with which the lens is to be worn. This step b) may be performed within the device via a window that is displayed on the display means 2 of the device 100. In a variant, it may be performed on the ophthalmologist's personal computer 22.

Thereafter, once said data has been input by the ophthalmologist, the method comprises a step c) of determining characteristics of the contact lens on the basis firstly of measurement data from the auto refractometer as previously stored, and secondly of the data previously input by the user in step b).

Thereafter, in a step d), the location of the contact lens within the cabinet 1 is identified.

Theater, in a step e), the box containing the contact lens is extracted from the cabinet 1. When the cabinet 1 is in the form of an automatic dispenser of lens boxes, this dispensing is performed automatically so there is no need to previously inform the ophthalmologist of the location of the lens within the cabinet. Nevertheless, the ophthalmologist may indeed be so informed.

In contrast, when the cabinet is in the form of a piece of furniture with drawers, as shown in FIG. 1, then an additional step is provided between steps d) and e) in which the ophthalmologist is informed of the location of the contact lens within the cabinet 1.

A step in which information contained on the box of the contact lens is identified (scanned), which box is provided for this purpose with a bar code or with an RFID chip.

In order to ensure that the contact lenses are restocked, the method may include the following steps. The information identified on the contact lens box is transmitted remotely, e.g. using the Internet, so as to enable the contact lenses to be restocked.

The data about the number of boxes of contact lenses having the same characteristics is thus known to the supplier via a remote server 40. The supplier can then decide to restock the contact lenses when desirable. The supplier may also manage this restocking in automatic manner by initiating restocking of contact lenses when the number of boxes including identified contact lenses as transmitted remotely drops below a predefined threshold value.

It should be observed that in practice the ophthalmologist does not need to perform the above-described method. The ophthalmologist is thus free to request or not request the transfer of data from the personal computer 22 to the device 100.

A step consisting in transmitting the characteristic data of the scanned lens to the ophthalmologist's personal computer may be envisaged. As explained above, this makes it possible to track the contact lenses that have been proposed to the patient.

Furthermore, it may turn out that the lens determined by the calculation performed by the calculation module 51 does not exist in the range of lenses available from the supplier, for example it may be a non-standard lens requiring made-to-measure fabrication or it may be a contact lens of a type that a priori is of "standard" type but that does not satisfy all of the criteria 1) to 8). Under such circumstances, step c) does not enable the contact lens to be determined from the range of lenses available from the supplier. At the end of steps a) to c), the user is then informed of the absence of this lens. The ophthalmologist can then order it using the device 100 to transmit a request remotely to the supplier.

It should also be observed that the remote link between the device 100 on the premises of the ophthalmologist and the remote server 40 on the premises of the contact lens supplier makes it possible to perform remote management of possible computer problems that might be encountered in the operation of the device 100.

Likewise, because of this remote link, it is possible to update the calculation module 51. By way of example, this may be useful when the supplier seeks to modify the type of standard contact lenses that are available in the cabinet, in agreement with the ophthalmologist, or indeed when it is decided to arrange these contact lenses differently in order to satisfy a particular desire of the ophthalmologist.

Finally, as mentioned above, it is possible to perform checking a few hours or a few weeks after the patient has tested the contact lens.

To this end, the method of the invention may also comprise the following steps:

f) at least measuring over refraction on a patient wearing the contact lens of characteristics that were determined at step c);

g) determining the characteristics of the new contact lens on the basis firstly of the measurement data obtained in step f) and secondly of the characteristics of the contact lens as determined in step c);

h) identifying the location within the cabinet (1) of the new contact lens; and i) extracting from the cabinet (1) the box containing the new contact lens.

Furthermore, if the contact lens of characteristics that were determined in step c) is a spherical lens, then step g) consists in determining the sphere, the cylinder and the axis of the new contact lens.

If the contact lens of characteristics that were determined in step c) is a toric lens, then step f) consists in performing at least over refraction measurement and a rotation measurement, and step g) consists in determining the sphere, the cylinder, and the axis of the new contact lens.

If the contact lens of characteristics that were determined in step c) is a progressive lens, then step f) consists in performing over refraction, duochrome, and near and far vision visual acuity measurements, in determining the dominant or fellow eye of the patient, and in providing the patient's age, and step g) consists in determining the sphere and/or the addition of the new contact lens.

The invention claimed is:

1. A device for selecting contact lenses within a cabinet arranged to receive a plurality of contact lenses, the device comprising:
   means for storing data based on measurements from an auto refractometer; and
   data processor means associated with a calculation module for identifying a contact lens on the basis firstly of data from the auto refractometer as previously stored in the storage means, and secondly of additional data relating to the contact lens that is to be identified and that was previously input by the user, said data processor means associated with said calculation module also being arranged to identify the location of the lens within the cabinet, wherein the data processor means associated with the calculation module are also arranged to determine the characteristics of a new lens from the characteristics of a previously identified lens and from additional data measured by the user on a patient wearing said previously identified lens, the additional data comprising at least a measurement of over refraction, said data processor means associated with said calculation module also being arranged to identify the location of this new lens within the cabinet, and wherein when said previously identified lens is a spherical lens, the data processor means associated with the calculation module are arranged to determine the sphere, the cylinder, and the axis of the new lens on the basis of the characteristics of the previously identified lens and of a measurement of over refraction performed on the patient wearing said previously identified lens.

2. A device according to claim 1, wherein the device includes means for identifying information relating to the content of a box including a contact lens in the identified location in the cabinet, which means are associated with a module for taking account of this data within the device.

3. A device according to claim 2, wherein the device comprises:
   remote transmission means for taking information relating to the contact lens for which the box has been identified and transmitting it remotely; and
   a remote computer server capable of communicating with the transmission means for remotely transmitting the information relating to the contact lens, the server being arranged to keep track of the contact lenses extracted from the cabinet.

4. A device according to claim 3, wherein the calculation module is incorporated in the remote computer server.

5. A device according to claim 1, wherein the calculation module is housed in the cabinet.

6. A device according to claim 1, wherein the means for identifying information relating to the content of a box containing the contact lens are arranged inside the cabinet, advantageously at an outlet from the cabinet.

7. A device according to claim 1, wherein the device includes display device for displaying said additional data relating to the contact lens, which data includes data to be supplied by a user concerning the shape of the lens, the nature of the material forming the lens, and the frequency with which the lens is to be worn.

8. A device according to claim 1, wherein the device includes a communications device for communicating with a personal computer of the user, which computer stores the data from the auto refractometer.

9. A device according to claim 1, wherein the cabinet has a plurality of drawers, each drawer being arranged to receive a plurality of series of contact lenses of a given model so that each series of contact lenses differs from another series of contact lenses by its ophthalmic correction power.

10. A device for selecting contact lenses within a cabinet arranged to receive a plurality of contact lenses, the device comprising:
    means for storing data based on measurements from an auto refractometer; and
    data processor means associated with a calculation module for identifying a contact lens on the basis firstly of data from the auto refractometer as previously stored in the storage means, and secondly of additional data relating to the contact lens that is to be identified and that was previously input by the user, said data processor means associated with said calculation module also being arranged to identify the location of the lens within the cabinet, wherein the data processor means associated with the calculation module are also arranged to determine the characteristics of a new lens from the characteristics of a previously identified lens and from additional data measured by the user on a patient wearing said previously identified lens, the additional data comprising at least a measurement of over refraction, said data processor means associated with said calculation module also being arranged to identify the location of this new lens within the cabinet, and wherein, when the previously identified lens is a tonic lens, the data processor means associated with the calculation module are arranged to determine the sphere, the cylinder, and the axis of the new lens from the characteristics of the previously identified lens and from measurements of over refraction and of rotation performed by the user on the patient wearing said previously identified lens.

11. A device for selecting contact lenses within a cabinet arranged to receive a plurality of contact lenses, the device comprising:
    means for storing data based on measurements from an auto refractometer; and
    data processor means associated with a calculation module for identifying a contact lens on the basis firstly of data from the auto refractometer as previously stored in the storage means, and secondly of additional data relating to the contact lens that is to be identified and that was previously input by the user, said data processor means associated with said calculation module also being arranged to identify the location of the lens within the cabinet, wherein the data processor means associated with the calculation module are also arranged to determine the characteristics of a new lens from the characteristics of a previously identified lens and from additional data measured by the user on a patient wearing said previously identified lens, the additional data comprising at least a measurement of over refraction, said data processor means associated with said calculation module also being arranged to identify the location of this new lens within the cabinet, and wherein, when the previously identified lens is a progressive lens, the data processor means associated with the calculation module are arranged to determine the sphere and/or the addition of the new lens from the characteristics of the previously identified lens, in particular its addition, from the age of the patient, and from over refraction, duochrome, and near and far vision visual acuity measurements, and from a determination of the dominant or fellow eye of the patient performed by the user on the patient wearing the previously identified lens.

12. A method of selecting contact lenses within a cabinet, the method comprising the following steps:
   a) storing data based on measurements from an auto refractometer;
   b) inputting additional data relating to the contact lens, other than the data provided by the auto refractometer, namely data relating to the shape of the lens, to the nature of the material forming the lens, and to the frequency with which the lens is to be worn;
   c) determining the characteristics of a contact lens available from the supplier on the basis firstly of measurement data from the auto refractometer that has previously been stored, and secondly from additional data previously input by the user in step b);
   d) identifying the location of the contact lens within the cabinet; and
   e) extracting the box including the contact lens from the cabinet.

13. A method according to claim 12, wherein the method further comprises the following steps:
   f) at least measuring over refraction on a patient wearing the contact lens of characteristics that were determined at step c);
   g) determining the characteristics of the new contact lens on the basis firstly of the measurement data obtained in step f) and secondly of the characteristics of the contact lens as determined in step c);
   h) identifying the location within the cabinet of the new contact lens; and
   i) extracting from the cabinet the box containing the new contact lens.

14. A method according to claim 13, wherein, when the contact lens of characteristics that were determined in step c) is a spherical lens, step g) consists in determining the sphere, the cylinder, and the axis of the new contact lens.

15. A method according to claim 13, wherein when the contact lens of characteristics that were determined in step c) is a toric lens, step f) consists at least in measuring over refraction and rotation, and step g) consists in determining the sphere, the cylinder, and the axis of the new contact lens.

16. A method according to claim 13, wherein when the contact lens of characteristics that were determined in step c) is a progressive lens, step f) consists in performing over refraction, duochrome, and near and far vision visual acuity measurements, in determining the dominant or fellow eye of the patient, and in providing the age of the patient, and step g) consists in determining the sphere and/or the addition of the new contact lens.

17. A method according to claim 16, wherein the method includes a step of informing the user of the location of the contact lens within the cabinet.

18. A method according to claim 12, wherein includes a step in which information contained on the box of the contact lens is identified, said box being provided with a bar code or with an RFID chip.

19. A method according to claim 12, wherein the method includes a step in which the information identified on the contact lens box is transmitted remotely in order to enable the contact lenses to be restocked.

20. A method according to claim 19, wherein the method includes a step in which restocking of contact lenses is initiated when the number of boxes including identified contact lenses as transmitted remotely drops below a predefined threshold value.

* * * * *

UNITED STATES PATENT AND TRADEMARK OFFICE
CERTIFICATE OF CORRECTION

PATENT NO.         : 9,282,885 B2
APPLICATION NO.    : 14/199368
DATED              : March 15, 2016
INVENTOR(S)        : Tamsot It is certified that error appears in the above-identified patent and that said Letters Patent is hereby corrected as shown below:

In the claims:

Column 18,
Line 26, claim 10 "tonic lens" should read --toric lens--.

Signed and Sealed this
Nineteenth Day of July, 2016

Michelle K. Lee
*Director of the United States Patent and Trademark Office*